US00PP22030P2

(12) United States Plant Patent
Hofmann

(10) Patent No.: US PP22,030 P2
(45) Date of Patent: Jul. 12, 2011

(54) ***DIASCIA* PLANT NAMED 'DEW DROPS'**

(50) Latin Name: *Diascia hybrida*
Varietal Denomination: Dew Drops

(75) Inventor: Silvia Hofmann, Mainz (DE)

(73) Assignee: InnovaPlant GmbH + Co. KG, Gensingen (DE)

( * ) Notice: Subject to any disclaimer, the term of this patent is extended or adjusted under 35 U.S.C. 154(b) by 0 days.

(21) Appl. No.: 12/798,718

(22) Filed: Apr. 10, 2010

(51) Int. Cl.
*A01H 5/00* (2006.01)

(52) U.S. Cl. ..... Plt./425

(58) Field of Classification Search ..... Plt./425
See application file for complete search history.

*Primary Examiner* — June Hwu
*Assistant Examiner* — Louanne C Krawczewicz Myers
(74) *Attorney, Agent, or Firm* — C. A. Whealy

(57) ABSTRACT

A new and distinct cultivar of *Diascia* plant named 'Dew Drops', characterized by its compact, outwardly spreading and mounding plant habit; freely branching habit; dense and bushy growth habit; early and freely flowering habit; white-colored flowers; and good garden performance.

1 Drawing Sheet

Botanical designation: *Diascia hybrida.*
Cultivar denomination: 'DEW DROPS'.

BACKGROUND OF THE INVENTION

The present invention relates to a new and distinct cultivar of *Diascia* plant, botanically known as *Diascia hybrida*, and hereinafter referred to by the name 'Dew Drops'.

The new *Diascia* plant is a product of a planned breeding program conducted by the Inventor in Gensingen, Germany. The objective of the breeding program is to create new compact and freely branching *Diascia* plants with early flowering habit, large flowers, attractive flower colors and good garden performance.

The new *Diascia* plant originated from an open-pollination during the summer of 2005 in Gensingen, Germany with *Diascia hybrida* 'Iceberg', not patented, as the female, or seed, parent with an unknown selection *Diascia hybrida*, as the male, or pollen, parent. The new *Diascia* plant was discovered and selected by the Inventor as a single flowering plant from within the progeny of the stated open-pollination in a controlled greenhouse environment in Gensingen, Germany in the late spring of 2006.

Asexual reproduction of the new *Diascia* plant by vegetative cuttings in a controlled greenhouse environment in Gensingen, Germany since 2006, has shown that the unique features of this new *Diascia* plant are stable and reproduced true to type in successive generations.

SUMMARY OF THE INVENTION

Plants of the new *Diascia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Dew Drops'. These characteristics in combination distinguish 'Dew Drops' as a new and distinct cultivar of *Diascia* plant:

1. Compact, outwardly spreading and mounding plant habit.
2. Freely branching habit; dense and bushy growth habit.

3. Early and freely flowering habit.
4. White-colored flowers.
5. Good garden performance.

Plants of the new *Diascia* can be compared to plants of the female parent, 'Iceberg'. Plants of the new *Diascia* differ from plants of 'Iceberg' in the following characteristics:

1. Plants of the new *Diascia* are more compact than plants of 'Iceberg'.
2. Plants of the new *Diascia* are more freely branching and bushier than plants of 'Iceberg'.
3. Plants of the new *Diascia* and 'Iceberg' differ in flower color as plants of 'Iceberg' have off white-colored flowers.

Plants of the new *Diascia* can be compared to plants of the *Diascia hybrida* 'Icepole', disclosed in U.S. Plant Pat. No. 14,503. In side-by-side comparisons conducted in Gensingen, Germany, plants of the new *Diascia* differed from plants of 'Icepole' in the following characteristics:

1. Plants of the new *Diascia* were denser and fuller than plants of 'Icepole'.
2. Plants of the new *Diascia* were more freely flowering than plants of 'Icepole'.
3. Plants of the new *Diascia* were more high temperature tolerant than plants of 'Icepole'.

BRIEF DESCRIPTION OF THE PHOTOGRAPHS

The accompanying colored photographs illustrate the overall appearance of the new *Diascia* plant, showing the colors as true as it is reasonably possible to obtain in colored reproductions of this type. Colors in the photographs may differ slightly from the color values cited in the detailed botanical description which accurately describe the colors of the new *Diascia* plant.

The photograph at the bottom of the sheet is a side perspective view of a typical flowering plant of 'Dew Drops' grown in a container.

The photograph at the top of the sheet is a close-up view of a typical flowering plant of 'Dew Drops'.

DETAILED BOTANICAL DESCRIPTION

The aforementioned photographs and following observations, measurements and values describe plants grown during the winter in 15-cm containers in a polyethylene-covered greenhouse in Bonsall, Calif. and under conditions which closely approximate commercial *Diascia* production. During the production of the plants, day temperatures averaged 24° C., night temperatures averaged 20° C. and light levels ranged from 5,000 to 6,000 foot-candles. Plants were pinched two times and were eight weeks old when the photographs and description were taken. In the following description, color references are made to The Royal Horticultural Society Colour Chart, 2007 Edition, except where general terms of ordinary dictionary significance are used.

Botanical classification: *Diascia hybrida* 'Dew Drops'.

Parentage:

*Female, or seed, parent.*—*Diascia hybrida* 'Iceberg', not patented.

*Male or pollen parent.*—Unknown selection of *Diascia hybrida*, not patented.

Propagation:

*Type.*—By vegetative cuttings.

*Time to initiate roots, summer.*—About ten days at 20° C.

*Time to initiate roots, winter.*—About two weeks at 20° C.

*Time to produce a rooted young plant, summer.*—About two weeks at 20° C.

*Time to produce a rooted young plant, winter.*—About two to three weeks at 20° C.

*Root description.*—Fine; white in color.

*Rooting habit.*—Freely branching.

Plant description:

*Plant form and growth habit.*—Compact, outwardly spreading and mounding plant habit; vigorous growth habit.

*Branching habit.*—Freely branching habit; dense and bushy growth habit; about six to eight primary lateral branches, each primary lateral branch with typically two secondary lateral branches developing at every node.

*Plant height.*—About 20 cm.

*Plant diameter* (*area of spread*).—About 54 cm.

Lateral branch description:

*Length.*—About 26 cm.

*Diameter.*—About 2 mm.

*Internode length.*—About 2.3 cm to 2.5 cm.

*Texture.*—Smooth, glabrous; longitudinally ridged.

*Color.*—Close to 146B.

Foliage description:

*Arrangement.*—Opposite, simple.

*Length.*—About 2.5 cm.

*Width.*—About 1.6 cm.

*Shape.*—Narrowly deltoid to broadly lanceolate.

*Apex.*—Acute.

*Base.*—Truncate to slightly cordate.

*Margin.*—Serrate.

*Texture, upper and lower surfaces.*—Smooth, glabrous.

*Venation pattern.*—Pinnate; arcuate.

*Color.*—Developing leaves, upper surface: Close to N137C. Developing leaves, lower surface: Close to 146B. Fully expanded leaves, upper surface: Close to N137C; venation, close to N137C. Fully expanded leaves, lower surface: Close to 147B; venation, close to 147C.

*Petiole.*—Length: About 3 mm. Diameter: About 1 mm. Texture, upper and lower surfaces: Smooth, glabrous. Color, upper surface: Close to 146B. Color, lower surface: Close to 147C.

Flower description:

*Flower arrangement and habit.*—Single flowers arranged on terminal racemes; flowers zygomorphic with five lobes fused at the base and twin-spurred; freely flowering habit with usually about 12 to 15 open flowers and flower buds per raceme; flowers face upright and outwardly.

*Fragrance.*—None detected.

*Flowering response and natural flowering season.*—Early flowering habit, plants begin flowering about three to four weeks after planting; flower freely and continuously from the spring into the fall in Southern California.

*Flower longevity.*—Flowers last about five to seven days on the plant; flowers not persistent.

*Inflorescence height.*—About 9.5 cm.

*Inflorescence diameter.*—About 3.4 cm.

*Flower diameter.*—About 1.8 cm by 2.1 cm.

*Flower depth.*—About 8 mm.

*Flower bud.*—Length: About 5 mm. Diameter: About 8 mm. Shape: Round to oval. Color: Close to NN155A.

*Corolla.*—Arrangement: Corolla consists of five petals modified into two upright banner petals, two lateral petals with spurs and a protruding lower lip petal. Banner lobe length: About 5 mm. Banner lobe width: About 5 mm. Lateral lobe length: About 6 mm. Lateral lobe width: About 7 mm. Lower lobe length: About 1.1 cm. Lower lobe width: About 1.5 cm. Banner, lateral and lower lobe shape: Orbicular to oval. Banner, lateral and lower lobe apex: Rounded. Banner, lateral and lower lobe margin: Entire. Banner, lateral and lower petal texture, upper and lower surfaces: Smooth, glabrous. Spur length: About 3 mm. Spur diameter: About 2 mm. Spur orientation: Curved downward. Color, banner, lateral and lower petals: When opening, upper and lower surfaces: Close to NN155C. Fully developed, upper surface: Close to NN155D; towards the base of the banner lobes, eye-spot, close to 5C. Fully developed, lower surface: Close to NN155C. Spurs: Close to NN155C; towards the apices, close to 157D.

*Sepals.*—Appearance: Five sepals fused into a star-shaped calyx. Length: About 2 mm. Width: About 1 mm. Shape: Lanceolate. Apex: Acute. Margin: Entire. Texture, upper surface: Smooth, glabrous. Texture, lower surface: Pubescent. Color, upper and lower surfaces: Close to 144A.

*Peduncles.*—Length: About 4.4 cm. Diameter: About 1.5 mm. Angle: Erect to about 45° from vertical. Texture: Sparsely pubescent. Color: Close to 146B.

*Pedicels.*—Length: About 1 cm. Diameter: Less than 1 mm. Angle: About 45° from the peduncle axis. Texture: Sparsely pubescent. Color: Close to 146B.

*Reproductive organs.*—Androecium: Stamen number per flower: About four. Filament length: About 2 mm. Filament color: Close to 145D. Anther shape: Ovoid. Anther length: About 1 mm. Anther color: Close to 13A. Amount of pollen: Scarce. Pollen color: Close to 12A. Gynoecium: Pistil number per flower: One. Pistil length: About 3 mm. Style length: About 1 mm. Style color: Close to 145B. Stigma color: Close to 145C. Ovary color: Close to N144A.

*Seed/fruit.*—Seed and fruit production have not been observed.

Garden performance: Plants of the new *Diascia* have been observed to have good garden performance and tolerate rain, wind and temperatures ranging from about 2° C. to about 35° C.

Pathogen/pest resistance: Plants of the new *Diascia* have not been shown to be resistant to pathogens and pests common to *Diascia*.

It is claimed:

1. A new and distinct *Diascia* plant named 'Dew Drops' as illustrated and described.

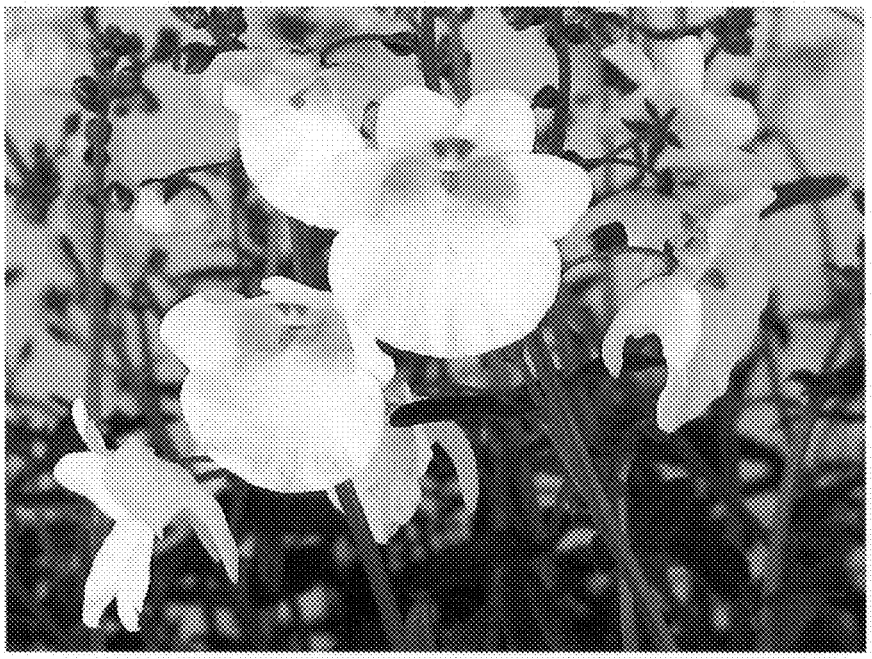
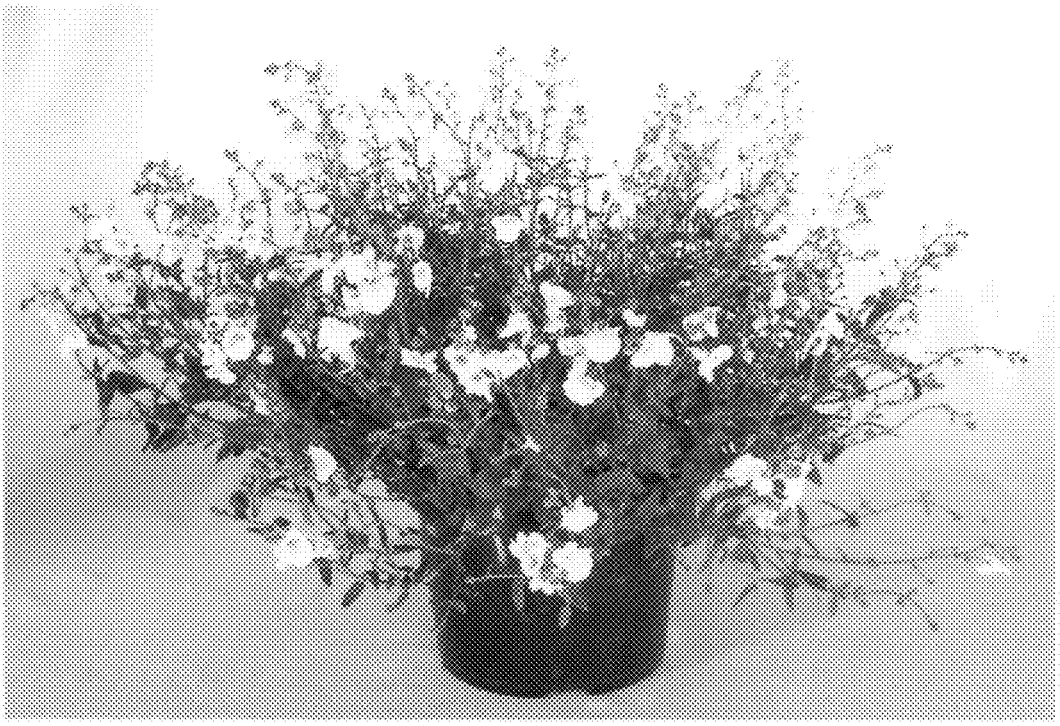

* * * * *